(12) United States Patent
Ikebukuro et al.

(10) Patent No.: US 9,238,816 B2
(45) Date of Patent: Jan. 19, 2016

(54) AMYLOID PROTEIN OLIGOMER-BINDING APTAMER

(75) Inventors: Kazunori Ikebukuro, Tokyo (JP); Kaori Tsukakoshi, Saitama (JP); Koji Sode, Tokyo (JP)

(73) Assignee: NATIONAL UNIVERSITY CORPORATION TOKYO UNIVERSITY OF AGRICULTURE AND TECHNOLOGY, Tokyo (JP)

( * ) Notice: Subject to any disclaimer, the term of this patent is extended or adjusted under 35 U.S.C. 154(b) by 199 days.

(21) Appl. No.: 14/000,190

(22) PCT Filed: Feb. 20, 2012

(86) PCT No.: PCT/JP2012/054017
§ 371 (c)(1),
(2), (4) Date: Sep. 16, 2013

(87) PCT Pub. No.: WO2012/111842
PCT Pub. Date: Aug. 23, 2012

(65) Prior Publication Data
US 2014/0072986 A1    Mar. 13, 2014

(30) Foreign Application Priority Data

Feb. 18, 2011  (JP) ................................. 2011-033998

(51) Int. Cl.
*C12N 15/115*    (2010.01)
*G01N 33/68*    (2006.01)

(52) U.S. Cl.
CPC .......... *C12N 15/115* (2013.01); *G01N 33/6896* (2013.01); *C12N 2310/16* (2013.01); *C12N 2310/50* (2013.01)

(58) Field of Classification Search
None
See application file for complete search history.

(56) References Cited

U.S. PATENT DOCUMENTS

| | | |
|---|---|---|
| 2008/0095706 A1 | 4/2008 | Orser et al. |
| 2009/0017040 A1 | 1/2009 | Pfeifer et al. |
| 2009/0017041 A1 | 1/2009 | Pfeifer et al. |
| 2010/0266576 A1 | 10/2010 | Rougeon et al. |
| 2010/0284934 A1 | 11/2010 | El-Agnaf |
| 2012/0171216 A1 | 7/2012 | Pfeifer et al. |
| 2013/0108549 A1 | 5/2013 | Orser et al. |

FOREIGN PATENT DOCUMENTS

| | | |
|---|---|---|
| JP | 2010-502938 A | 1/2010 |
| JP | 2010-530227 A | 9/2010 |
| JP | 2010-531992 A | 9/2010 |
| JP | 2010-537962 A | 12/2010 |
| WO | 2004/042083 A2 | 5/2004 |

OTHER PUBLICATIONS

Mashima, et al., "Unique quadruplex structure and interaction of an RNA aptamer against bovine prion protein," *Nucleic Acids Research*, vol. 37, No. 18, pp. 6249-6258 (2009).
Murakami, et al., "Anti-bovine prion protein RNA aptamer containing tandem GGA repeat interacts both with recombinant bovine prion protein and its β isoform with high affinity," *Prion*, vol. 2, No. 2, pp. 73-80 (2008).
Sekiya, et al., "In vitro selection of RNA aptamers against cellular and abnormal isoform of mouse prion protein," *Nucleic Acids Symposium Series*, vol. 49, pp. 361-362 (2005).
Tsukakoshi, et al., "Development of DNA aptamers that bind to amyloid oligomers," *Alzheimer's & Dementia*, vol. 7, No. 4, p. S331 (2011).
Weiss, et al., "RNA Aptamers Specifically Interact with the Prion Protein PrP," *Journal of Virology*, vol. 71, No. 11, pp. 8790-8797 (1997).
European Search Report for corresponding EP Application No. 12747811.3 dated Sep. 22, 2014, 12 pages.
"Saibo Shogaisei Oligomer Kenshutsu ni Muketa α-synuclein Ketsugo DNA Aptamer no Tansaku", Kaori et al., 2010 Fall Meeting of the Electrochemical Society of Japan, Meeting Abstracts, p. 159.
Office Action for Chinese Application No. 201280008801.1, with English translation, dated Jan. 4, 2015, 10 pages.
Tsukakoshi, et al., "Screening of DNA aptamer which binds to α-synuclein," *Biotechnol. Lett.*, vol. 32, pp. 643-648 (2010).
Tsukakoshi, et al., "The screening of DNA aptamers which specifically bind to α synuclein for determination of the cytotoxic oligomers," *Abstracts of Autumn Meeting of the Electrochemical Society of Japan*, p. 159, 2H33 (2010).
Response to Written Opinion of the ISA for International Application No. PCT/JP2012/054017, dated Mar. 13, 2012.
International Search Report for International Application No. PCT/JP2012/054017, 2 pages, mailed Mar. 13, 2012.

Primary Examiner — Gregory S Emch
(74) Attorney, Agent, or Firm — Kilpatrick Townsend & Stockton LLP

(57) ABSTRACT

An aptamer having a G-quartet structure and being at least one selected from the group consisting of the following polynucleotides, the aptamer having a binding ability to an amyloid protein oligomer: (1) a polynucleotide comprising a base sequence represented by any one of SEQ ID NO:1 to SEQ ID NO:18; (2) a polynucleotide comprising a base sequence that includes at least four sets of at least two consecutive guanosine nucleotides and in which one or several bases has been deleted, substituted, or added in a base sequence represented by any one of SEQ ID NO:18; and (3) a polynucleotide that is a multimer including the polynucleotide of (1) or (2) as a structural unit.

12 Claims, 6 Drawing Sheets

FIG.1

|         | M | O | F |         | M | O | F |
|---------|---|---|---|---------|---|---|---|
| T-SO517 |   | ● | · |  T-SO606 |   | ● |   |
| T-SO504 |   | ● | · |  T-SO508 |   | ● |   |
| T-SO554 |   | ● |   |  T-SO552 |   | ● |   |
| T-SO530 |   | ● | · |  T-SO602 |   | ● |   |

(M; Monomer, O; Oligomer, F; Fibril)

FIG.2

|         | P | C | L | A | O |
|---------|---|---|---|---|---|
| A11     |   | · |   | · | ● |
| T-SO517 |   |   |   |   | ● |
| T-SO606 |   |   |   |   | ● |

P; PQQGDH, C; C-reactive protein, L; Luciferase,
A; Antibody (IgG), O; oligomer

FIG.3

| | A$\beta_{1-40}$ | | |
| --- | --- | --- | --- |
| | M | O | F |
| T-SO517 | | ● | |
| T-SO504 | | ● | |
| T-SO606 | | ● | |
| T-SO508 | | ● | |
| T-SO552 | | ● | |
| T-SO530 | | ● | |
| T-SO554 | | ● | |
| T-SO602 | | ● | |
| A11 | | ● | |

(M; Monomer, O; Oligomer, F; Fibril)

(M; Monomer, O; Oligomer, F; Fibril)

(M; Monomer, O; Oligomer, F; Fibril)

AMYLOID PROTEIN OLIGOMER-BINDING APTAMER

CROSS-REFERENCE TO RELATED APPLICATIONS

This application is the U.S. National Stage entry of PCT/JP2012/054017, filed Feb. 20, 2012, which claims benefit of Japanese Patent Application No. 2011-033998, filed Feb. 18, 2011, the disclosures of each are herein incorporated by reference.

TECHNICAL FIELD

The present invention relates to an amyloid protein oligomer-binding aptamer and use thereof.

BACKGROUND ART

α-synuclein (α-Syn) is a main constituent protein of an inclusion body found in Parkinson's disease (PD) and dementia with Lewy bodies (DLB). The protein is thought to acquire cytotoxicity by aggregation to cause disease. α-synuclein oligomer, which is an aggregation intermediate of α-Syn, is reported to exhibit higher cytotoxicity than amyloid fibril as a final product. It is thus suggested that the α-synuclein oligomer is likely to be a main body of toxicity causing PD and DLB.

In addition, not limited to α-synuclein, accumulations of amyloid proteins such as β amyloid peptide and tau protein, prion protein, polyglutamine peptide, and huntingtin, respectively, are significantly associated with the occurrence of diseases such as Alzheimer's disease, prion disease, polyglutamine disease, and Huntington's disease, respectively. These proteins are also ever present in soluble forms in the body and change their conformations due to some stimuli to form oligomers, then resulting in amyloid fibril formation in insoluble forms.

Regarding diseases caused by depositions or the like of these proteins, specific detection of amyloid protein oligomer is needed to elucidate the pathogenesis of the diseases. Additionally, knowing the localization of the oligomers in tissues is useful for the prevention and diagnosis of such diseases.

Accordingly, various techniques have been developed to specifically detect oligomeric amyloid proteins. For example, Japanese Unexamined Patent Application Publication (JP-A) Nos. 2010-531992 and 2010-530227 disclose anti-amyloid β peptide antibodies. In addition, JP-A Nos. 2010-502938 and 2010-537962 disclose anti-amyloid β protein monoclonal antibodies.

Meanwhile, an aptamer is known as a polynucleotide molecule that specifically binds to a certain molecule. Aptamers can be totally chemically synthesized using a commercially available nucleic acid synthesizer and thus are advantageous in terms of obtaining at much lower cost than specific antibodies and allowing the designing of structural changes due to easy modification. Furthermore, unlike peptides, aptamers return to their original state even when denatured at high temperature and therefore are highly stable. Aptamers form a specific three-dimensional structure to have a molecular recognition ability selective to a target molecule. As the three-dimensional structure of aptamers, various shapes have been reported, such as those of hairpin, pseudoknot, bulge, and G-quartet.

As an aptamer for detecting α-synuclein, M5-15 is known, which has plural hairpin structures (see Biotechnol. Lett., (2010) vol. 32, pp. 643-648). The α-synuclein-binding aptamer M5-15 is described to recognize not only synuclein oligomer but also α-synuclein monomer.

SUMMARY OF INVENTION

As described above, there has been a desire for specific recognition of an amyloid protein oligomer. However, no useful aptamer has been obtained to specifically recognize an amyloid protein oligomer.

Therefore, it is an object of the present invention to provide an aptamer capable of specifically recognizing an amyloid protein oligomer and an amyloid protein oligomer detection method using the same.

The present invention provides the following aspects:
[1] An aptamer having a G-quartet structure and being at least one selected from the group consisting of the following polynucleotides, the aptamer having a binding ability to an amyloid protein oligomer:
(1) a polynucleotide including a base sequence represented by any one of SEQ ID NO:1 to SEQ ID NO:18;
(2) a polynucleotide including a base sequence that includes at least four sets of at least two consecutive guanosine nucleotides and in which one or several bases has been deleted, substituted, or added in a base sequence represented by any one of SEQ ID NO:1 to SEQ ID NO:18; and
(3) a polynucleotide that is a multimer including the polynucleotide of (1) or (2) as a structural unit.
[2] The aptamer according to [1], in which the polynucleotide (3) includes the polynucleotide of (1) or (2) and a linker sequence linking respective polynucleotides of (1) or (2).
[3] An amyloid protein oligomer detection kit including the aptamer according to [1] or [2].
[4] An amyloid protein oligomer detection method, the method including contacting the aptamer according to [1] or [2] with a test sample and detecting a complex of an amyloid protein oligomer and the aptamer in the test sample.
[5] The amyloid protein oligomer detection method according to [4], in which the test sample is at least one selected from the group consisting of cerebrospinal fluid, serum, plasma, and dilutions thereof.
[6] A polynucleotide comprising a base sequence represented by any one of SEQ ID NO:1 to SEQ ID NO:18.
[7] A multimeric polynucleotide that is a multimer including, as a structural unit, a polynucleotide including a base sequence represented by any one of SEQ ID NO:1 to SEQ ID NO:18.

Advantageous Effects

The present invention can provide an aptamer capable of specifically recognizing an amyloid protein oligomer and an amyloid protein oligomer detection method using the same.

BRIEF DESCRIPTION OF DRAWINGS

FIG. 1 are views illustrating the results of an aptamer blotting assay for comparing the binding ability of respective aptamers according to Example 1 to α-synuclein monomer, oligomer, or fibril.

FIG. 2 is a view illustrating the results of an aptamer blotting assay for comparing the binding ability of the respective aptamers according to Example 1 to various proteins.

FIG. 3 is a view illustrating the results of an aptamer blotting assay for comparing the binding ability of the respective aptamers according to Example 1 to β amyloid peptide $A\beta_{1-40}$

DESCRIPTION OF EMBODIMENTS

Figure 4:
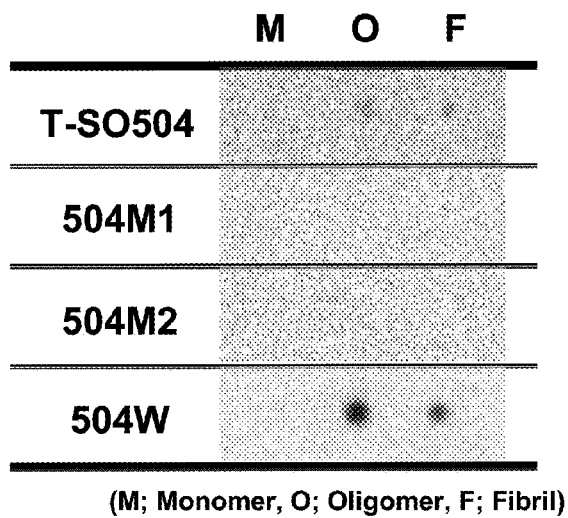
FIG. 4 is a view illustrating the results of an aptamer blotting assay for comparing the binding ability of respective aptamers according to Example 2 to α-synuclein monomer, oligomer, or fibril.

An aptamer of the present invention is a polynucleotide having a G-quartet structure and is at least one selected from the group consisting of the following polynucleotides, the aptamer having a binding ability to an amyloid protein oligomer:

(1) a polynucleotide including a base sequence represented by any one of SEQ ID NO:1 to SEQ ID NO:18;

(2) a polynucleotide including a base sequence that includes at least four sets of at least two consecutive guanosine nucleotides and in which one or several bases has been deleted, substituted, or added in a base sequence represented by any one of SEQ ID NOs: 1 to 18; and (3) a polynucleotide including the polynucleotide of (1) or (2) as at least a dimer or a larger multimer.

The aptamer having the binding ability to an amyloid protein oligomer according to the present invention (hereinafter referred to as an "amyloid protein oligomer-binding aptamer") is an aptamer that has a specific base sequence or a base sequence similar thereto and a G-quartet structure. Thus, the aptamer can specifically recognize the oligomer and can bind thereto according to the conformational change of amyloid protein.

More specifically, as described above, amyloid protein changes its conformation into a monomer type, an oligomer type, and a fibril type. In the present invention, it has been found that the above specific aptamer having a G-quartet structure has different binding abilities with respect to the oligomer type and the monomer type. Use of the G-quartet type aptamer as above allows the specific recognition of an oligomeric amyloid protein.

The specificity of the amyloid protein oligomer-binding aptamer means a specificity that allows the discrimination of amyloid proteins from proteins other than amyloid proteins and allows the discrimination between an amyloid protein monomer and an amyloid protein oligomer. In addition, the amyloid protein oligomer-binding aptamer may have a binding ability to an amyloid protein fibril.

The term "aptamer" in the present specification represents a nucleic acid ligand that binds to a specific molecule.

The term "process" in the present invention encompasses not only an independent process but a process that is not clearly discriminated from other processes as long as an intended effect of the process is achieved.

In addition, a numerical range indicated using "to" in the present specification represents a range including numerical values described before and after "to" as a minimum value and a maximum value, respectively.

Additionally, in the present invention, when referring to an amount of each component included in a composition, if a substance corresponding to the each component is present in plurality in the composition, the amount thereof in the composition means a total amount of the plural substances present in the composition unless otherwise stated.

Hereinbelow, the present invention will be described.

<Amyloid Protein Oligomer-Binding Aptamer>

The amyloid protein-binding aptamer of the present invention is a polynucleotide having a G-quartet structure and is at least one selected from the group consisting of the following polynucleotides, the aptamer having a binding ability to an amyloid protein oligomer:

(1) a polynucleotide including a base sequence represented by any one of SEQ ID NO:1 to SEQ ID NO:18;

(2) a polynucleotide including a base sequence that includes at least four sets of at least two consecutive guanosine nucleotides and in which one or several bases has been deleted, substituted, or added in a base sequence represented by any one of SEQ ID NOs: 1 to 18; and (3) a polynucleotide that is at least a dimer or a larger multimer including the polynucleotide of (1) or (2).

Such base sequences have a G-quartet structure and thus allow the specific recognition of an amyloid protein oligomer.

| | | |
|---|---|---|
| T-S0517: | GGTGGCTGGAGGGGGCGCGAACG | (SEQ ID NO: 1) |
| T-S0606: | GGGTCGGCTGTCCGTGGGTGGGGA | (SEQ ID NO: 2) |
| T-S0554: | CGAGGGGCGTCTGGGAGTGGTCGG | (SEQ ID NO: 3) |
| T-S0530: | GGTGCGGCGGGACTAGTGGGTGTG | (SEQ ID NO: 4) |
| T-S0552: | GCGTGTGGGGCTTGGGCAGCTGGG | (SEQ ID NO: 5) |
| T-S0504: | CAGGGGTGGGCAAAGGGCGGTGGTG | (SEQ ID NO: 6) |
| T-S0508: | GCCTGTGGTGTTGGGGCGGGTGCG | (SEQ ID NO: 7) |
| T-S0602: | GCGGTAGGGTGTGAGCGGAAGGGG | (SEQ ID NO: 8) |
| 2G16: | CGAGGGGCGTCTGGGGGGGAGGGA | (SEQ ID NO: 9) |
| 2G4: | CGGGGGGCGTGTGGGAGAGGTCGG | (SEQ ID NO: 10) |
| 2G13: | TGGGGGGCGTAGGGTCGCGAACGA | (SEQ ID NO: 11) |
| 2G9: | CGGGGGGCGTAGGGGAGAGGGGCG | (SEQ ID NO: 12) |
| 3G4: | CGGGGGGCCTGAGGGGGGGAGGGA | (SEQ ID NO: 13) |
| 3G21: | CGGGGCGCATCTGGGGGGGAGGGA | (SEQ ID NO: 14) |
| 3G16: | CGGGGGGCTTGTGGCGGGGAGGGA | (SEQ ID NO: 15) |
| 3G22: | CGAGGGGAGTAGGGGGGAGGGGCG | (SEQ ID NO: 16) |
| 3G14: | CGGGGGGCGTCTGGGCGCGAGGGA | (SEQ ID NO: 17) |
| 3G9: | CGGGGGCCGTTGGGGGGGAGGGA | (SEQ ID NO: 18) |

The G-quartet structure is a structure well-known in the art. The structure is an intermolecular and intramolecular quadruplex structure formed in guanosine nucleotide (G)-rich DNA or RNA. The G-quartet structure is formed by connecting four guanosine bases to each other, in which a pair of the bases adjacent to each other forms two hydrogen bonds, in a ring-like structure through Hogsten hydrogen bonds. Finally, stacking of G-quartet structures results in a four molecular helical structure.

It can be confirmed by a known measurement means that an aptamer has a G-quartet structure. For example, by detecting a predetermined waveform using CD spectra, the aptamer can be confirmed to have the G-quartet structure. For example, an aptamer is dissolved in a TBS buffer solution (10 mM Tris-HCl, 150 mM NaCl, 5 mM KCl, and pH 7.4) to prepare a sample solution. Then, spectra measurement in the solution is performed under conditions of: a temperature of 20° C., a wavelength of from 200 nm to 320 nm, a scan rate of 100 nm/min, and an accumulated number of times of 10 times. Then, in CD spectra obtained under these conditions, the presence of a minimum value near 240 nm and a maximum value near 260 nm indicates that the aptamer has a G-quartet structure.

The kinds of nucleotides constituting the aptamer are not particularly limited as long as the kinds of bases included in the nucleotides may form a G-quartet structure. Examples of the kinds of the nucleotides include deoxyribonucleotides, ribonucleotides, and the like. In addition, the nucleotides in the aptamer of the present invention may also encompass pseudo-nucleic acids such as peptide nucleic acid. Additionally, the nucleotides may include a modified nucleotide. The nucleotides of the aptamer are preferably ribonucleotides, namely RNA, from the viewpoint of flexibility of the three-dimensional structure at the time of reaction of a target substance.

Examples of the modified nucleotide include modified nucleotides resistant to RNAase and labeled nucleotides for fluorescence detection. Examples of labels include already-known labels usable in this field, such as a fluorescent substance such as FITC, biotin, and avidin.

The aforementioned aptamer (2) is a polynucleotide including a base sequence that includes at least four sets of at least two consecutive guanosine nucleotides having a G-quartet structure and in which one or several bases has been deleted, substituted, or added in a base sequence represented by any one of SEQ ID NOs: 1 to 18. Such a polynucleotide may have a G-quartet structure and a binding ability to an amyloid protein oligomer, as in the polynucleotide consisting of the base sequence represented by any one of the SEQ ID NOs: 1 to 18 above.

The amyloid protein oligomer-binding aptamer has a nucleotide length of from 20 to 30 and preferably from 23 to 25 in terms of the binding ability to amyloid protein.

The aptamer (2) includes at least four sets of at least two consecutive guanosine nucleotides. The phrase "at least two consecutive guanosine nucleotides" means that two or more guanosine nucleotides continue in the sequence. In addition, the phrase "includes at least four sets" mean that four or more sets of at least two consecutive guanosine nucleotides are included in the sequence. Thus, for example, a series of four guanosine nucleotides means a series of two sets of two consecutive guanosine nucleotides. From the viewpoint of ensuring the G-quartet structure formation to reliably achieve amyloid protein oligomer recognition, it is preferable to include four sets of two or more consecutive guanosine nucleotides in the sequence. Furthermore, from the viewpoint of further ensuring amyloid protein oligomer recognition, the aptamer is preferably a polynucleotide that has a nucleotide length of from 23 to 25 and includes from 14 to 15 guanosine nucleotides in a sequence thereof.

As long as the conditions of the number of guanosine nucleotides in the aptamer (2) are satisfied and the aptamer may specifically bind to an oligomeric amyloid protein, in the amyloid protein oligomer-binding aptamer according to the present invention, one or several bases may be deleted, substituted or added in a base sequence represented by any one of SEQ ID NOs: 1 to 18. The several bases may be, for example, from two to five bases.

Such an amyloid protein-binding aptamer may specifically bind to an oligomeric amyloid protein.

In addition, as long as the conditions of the number of guanosine nucleotides in the aptamer (2) are satisfied and the aptamer may specifically bind to an oligomeric amyloid protein, the amyloid protein oligomer-binding aptamer according to the present invention may include a base sequence that is hybridized, under stringent conditions, with a base sequence complementary to a base sequence represented by any one of SEQ ID NOs: 1 to 18.

The stringent conditions herein refer to conditions in which a specific hybrid is formed and no non-specific hybrid is formed. Examples of typical stringent conditions include conditions in which hybridization is performed at a potassium concentration of from about 25 mM to about 50 mM and a magnesium concentration of from about 1.0 mM to about 5.0 mM.

The aptamer may be selected from a random polynucleotide library based on the binding ability to a target substance by performing in vitro screening using a process for the systemic evolution of ligands by exponential enrichment (SELEX).

In addition, regarding the obtained aptamer, the sequence of the aptamer is further optimized using, as an indication, the binding ability to an oligomeric amyloid protein, whereby other aptamers may be obtained. An example of the method for optimization is a so-called in silico maturation. The in silico maturation includes an operation for evaluation and ranking of aptamers in vitro and an operation for creating a novel sequence based on an evolution-mimicking algorithm in silico (in computer), such as sequence recombination and shuffling, and various mutation introductions. A combination of the two operations is referred to as one generation, and operations through some generations are repeated to acquire an aptamer sequence having an intended function (for example, see Nucleic Acids Res., (2005) vol. 33(12), pp. e108; Biochem Biophys Res Commun., (2006) vol. 347(1), pp. 226-31; Biosens Bioelectron., (2010) vol. 15; 26(4), pp. 1386-91).

In addition, an aptamer having an already-known sequence may be chemically synthesized by a usual method.

The binding ability of the obtained aptamer to an amyloid protein oligomer may be confirmed by a usual method such as blotting assay.

For example, blotting assay is performed as follows:

On a nitrocellulose membrane, from 0.5 μg to 1 μg of an amyloid protein oligomer is immobilized to prepare a membrane for blotting. A fluorescent substance (for example, FITC) is linked to an aptamer as a test object to prepare a sample aptamer.

To the blotting membrane prepared above is added a TBS-T solution (25 mM Tris-HCl, pH 7.4, 0.15 M NaCl, 0.005 M KCl, 0.05% Tween 20) containing the obtained sample aptamer at a concentration of from 50 nM to 5 μM, followed by incubating at room temperature for 1 hour. After that, the membrane is washed with a sufficient amount of TBS-T (2 min×twice and 10 min×one time).

The nitrocellulose membrane after washing is incubated at room temperature for 1 hour, together with an antibody (for example, an anti-FITC antibody) against the fluorescent substance modified with a detection enzyme (for example, HRP) diluted to 1000 times with TBS-T. Then, the membrane is washed with a sufficient amount of TBS-T (2 min×twice, 10 min×one time, and 5 min×twice).

Next, a substrate for the detection enzyme is added to detect chemiluminescence, thereby evaluating the binding of the sample aptamer to the amyloid protein oligomer.

Amyloid proteins recognizable by the amyloid protein-binding aptamer are those that are likely to cause conformational changes. Examples of such amyloid proteins include α-synuclein (an amyloid protein associated with Parkinson's disease), β amyloid peptide (an amyloid protein associated with Alzheimer's disease), prion protein (an amyloid protein associated with a so-called mad cow disease), tau protein (an amyloid protein associated with Alzheimer's disease), polyglutamine peptide (an amyloid protein associated with polyglutamine disease), and huntingtin (an amyloid protein associated with Huntington's disease) and the like.

The amyloid protein-binding aptamer can be a multimer (hereinafter referred to as a "multimeric aptamer") including the polynucleotide (1) or (2) as a structural unit. Such a multimeric aptamer may have a higher binding ability to an amyloid protein oligomer as compared to an aptamer including only the polynucleotide (1) or (2) (hereinafter referred to as a "structural unit") constituting the multimeric aptamer.

Examples of such a multimeric aptamer include, in addition to a dimeric aptamer including two of the structural unit linked to each other, a trimeric aptamer including three of the structural unit linked to each other, and a tetrameric aptamer including four of the structural unit linked to each other, a pentamer or a larger multimer, for example, formed by including from 10 to 30 of the structural units. In addition, such a multimeric aptamer may be formed in a range of from a dimer to roughly a tetrameter. If the aptamer is a dimer or larger, the binding ability thereof to an amyloid protein oligomer tends to be improved. In addition, if the aptamer is roughly tetrameric, an effect of improving the binding ability thereof to an amyloid protein oligomer that corresponds to the number of the structural units tends to be obtained.

The multimeric aptamer may be an aptamer including the structural units linked in tandem or a dendrimer type. In the case of the structural units linked in tandem, examples of a linking form include a form of linking the structural units in the same direction (namely, a (head-to-tail)-(head-to-tail) type) and a form of linking the structural units in opposite directions (namely, a (head-to-tail)-(tail-to-head) type). In the case of a dendrimer type, examples of the core include ethylenediamine and hexamethylenediamine.

In these multimeric oligomers, a linker sequence may be included between monomer units.

Examples of the linker sequence include sequences composed of two or more consecutive thymidine nucleotides or cytosine nucleotides, which are nucleotides other than guanosine nucleotides. The linker sequence may have a length of from 2 to 15, and preferably from 3 to 10 in terms of improving the bonding ability.

The amyloid protein-binding aptamer may be used alone or in a combination of two or more. Additionally, in the case of a multimeric aptamer, the aptamer may be a combination of aptamers including different numbers of the structural units.

In addition, the amyloid protein-binding aptamer may have an additional sequence at each end thereof. Examples of such an additional sequence include a sequence composed of two or more consecutive thymidine nucleotides or cytosine nucleotides, which are nucleotides other than guanosine nucleotides. Such an additional sequence may be provided, for example, in order to retain a function of a labeling substance at a labeled end of an oligonucleotide. Examples of the additional sequence include five consecutive thymidine nucleotides or adenine nucleotides and the like. Providing the five consecutive thymidine nucleotides may prevent, for example, the reduction of fluorescence intensity of a fluorescently labeled aptamer.

The amyloid protein-binding aptamer may be chemically synthesized according to a sequence using an already-known method, and those skilled in the art would be able to appropriately select a synthesis method for obtaining the amyloid protein-binding aptamer.

<Amyloid Protein Oligomer Detection Method>

An amyloid protein oligomer detection method of the present invention includes contacting the amyloid protein oligomer-binding aptamer with a body fluid sample (a contact process) and detecting a complex of the amyloid protein oligomer and the amyloid protein oligomer-binding aptamer in the body fluid sample (a detection process).

In the amyloid protein oligomer detection method, the amyloid protein oligomer-binding aptamer capable of specifically binding amyloid protein is contacted with an amyloid protein oligomer as a target molecule to detect a complex composed of the aptamer and the protein, so that the amyloid protein oligomer in the sample may be specifically detected.

The body fluid sample that is an object for detecting an amyloid protein oligomer is not particularly limited as long as the sample is a test sample that may contain the amyloid protein oligomer. Body fluid samples that can be used may include body fluids such as cerebrospinal fluid, serum, and plasma, and dilutions thereof. These test samples may be ones that have been separated from a test subject.

Before contacting the amyloid protein oligomer-binding aptamer with the test sample, a process of preparing the test sample may be provided. Examples of such a preparation process include collection from the test subject and dilution of a collected sample to a concentration suitable for detection using an appropriate diluting solution.

There is no particular limitation to the contact of the amyloid protein oligomer-binding aptamer with the test sample in the contact process, and conditions usually used to allow an aptamer to contact with a target molecule may be employed without any change. If a target amyloid protein oligomer is present in the test sample, a complex of the amyloid protein oligomer-binding aptamer and the target amyloid protein oligomer may be formed in the sample.

In the detection process, the complex formed in the contact process is detected. As used herein, the term "detection" in the present detection process encompasses not only detection of the absence or presence of the complex in the sample, but also quantitative determination of the complex in the sample. In addition, by using a calibration curve, from the detection or quantitative determination of the complex, detection or quantitative determination of the target amyloid protein oligomer in the sample may also be performed by a usual method.

The detection or quantitative determination of the target amyloid protein oligomer in the sample may be performed by a well-known usual method using an aptamer. Examples of the well-known method include immunoassay methods using aptamer instead of antibody (immunochromatography and enzyme-linked immunosorbent assay (ELISA)), measurement methods described in WO 2005/049826 and WO 2007/086403, an aptamer blotting method (Japanese Patent Application Laid-Open (JP-A) No. 2008-8237042), and surface plasmon resonance (SPR).

Amyloid protein oligomers detectable by the present detection method are, for example, oligomers of amyloid proteins that may cause conformational change. Examples of such amyloid proteins include α-synuclein (an amyloid protein associated with Parkinson's disease), β amyloid peptide (an amyloid protein associated with Alzheimer's disease), prion protein (an amyloid protein associated with a so-called mad cow disease), tau protein (an amyloid protein associated with Alzheimer's disease), polyglutamine peptide (an amyloid protein associated with polyglutamine disease), and huntingtin (an amyloid protein associated with Huntington's disease), as well as SODI protein, TDP-43 protein (protein associated with amyotrophic lateral sclerosis), amylin (protein associated with type II diabetes), plasma amyloid A protein, lysosome (protein associated with systemic amyloidosis), and β2-microglobulin (protein associated with dialysis amyloidosis).

<Amyloid Protein Oligomer Detection Kit>

An amyloid protein oligomer detection kit of the present invention includes the amyloid protein oligomer-binding aptamer.

The amyloid protein oligomer-binding aptamer included in the kit may, as described above, specifically detect an amyloid protein oligomer. Accordingly, use of the kit allows easy detection of an amyloid protein oligomer.

The kit may include a storage part storing the amyloid protein oligomer-binding aptamer and product descriptions explaining the amyloid protein oligomer detection method using the amyloid protein oligomer-binding aptamer. In addition, the kit may also include a diluent storage part storing a diluent for diluting a test sample as an object for detecting an amyloid protein oligomer to an appropriate concentration. In addition to this or instead of this, the kit may include a reagent storage part storing other reagents.

The term "storage part" in the kit is not particularly limited as long as the storage part has a configuration useful to allow respective reagents to be kept independent without being mixed together. For example, the storage part may be a container, an individually packaged form, or a single sheet form with independently partitioned regions.

Examples of other reagents that may be included in the kit include reagents usable to detect the complex and positive or negative control samples.

<Other Uses>

As descried above, the one aspect of the present invention provides (1) a polynucleotide including a base sequence represented by any one of SEQ ID NO:1 to SEQ ID NO:18, (2) a polynucleotide including a base sequence that includes at least four sets of at least two consecutive guanosine nucleotides and in which one or several bases has been deleted, substituted, or added in a base sequence represented by any one of SEQ ID NOs: 1 to 18, and (3) a multimeric polynucleotide including, as a structural unit, a polynucleotide including a base sequence represented by any one of SEQ ID NO:1 to SEQ ID NO:18.

The polynucleotides or the multimeric polynucleotide may be applicable to various uses other than the uses described above.

Particularly, the polynucleotides or the multimeric polynucleotide has the binding ability to specifically amyloid protein oligomer, as the amyloid protein oligomer-binding aptamer, and therefore can be used for various embodiments in which amyloid protein oligomers are targeted.

For example, the amyloid protein oligomer-binding aptamer may be applied as a therapeutic or prophylactic agent for a disease associated with the kind of a target amyloid protein oligomer or as a therapeutic or prophylactic pharmaceutical composition therefor. The therapeutic or prophylactic agent includes the amyloid protein oligomer-binding aptamer as an active ingredient. Additionally, the therapeutic or prophylactic pharmaceutical composition includes the amyloid protein oligomer-binding aptamer and a pharmaceutical acceptable carrier. Examples of the pharmaceutical acceptable carrier include various organic or inorganic carrier substances commonly used for that purpose. In a case of a therapeutic or prophylactic agent, or a therapeutic or prophylactic pharmaceutical composition, the amyloid protein oligomer-binding aptamer may further be included as a form of a conjugate with other therapeutic or prophylactic active ingredients.

In addition, the present invention also encompasses a therapeutic or prophylactic method for a disease associated with the kind of a target amyloid protein oligomer. The therapeutic or prophylactic method therefor includes administering an effective dose of the amyloid protein oligomer-binding aptamer to a target subject.

Examples of diseases targeted for the treatment or prevention include diseases associated with amyloid protein oligomers. Examples of such diseases include Alzheimer's disease, dementia with Lewy bodies, Parkinson's disease, multiple system atrophy, Creutzfeldt-Jakob disease, prion diseases such as bovine spongiform encephalopathy or scrapie, tauopathies such as Pick's disease and progressive supranuclear palsy, polyglutamine diseases such as Huntington's disease, amyotrophic lateral sclerosis, type II diabetes, and amyloidosis such as systemic amyloidosis and dialysis amyloidosis, and the like.

In addition, administration subjects may be any as long as the subjects are living things that can cause the accumulation of amyloid protein oligomer. Examples of the subjects include primates such as humans and monkeys, and domestic animals such as cows, horses, and sheep.

In addition, the amyloid protein oligomer-binding aptamers (1) to (3) each may be a constituent part of an aptamer-conductive particle conjugate including the amyloid protein oligomer-binding aptamer and conductive particles that may generate heat by high frequency induction heating.

As used herein, the term "high frequency induction heating" refers to heating at a predetermined temperature under heating conditions such as high frequency and high frequency voltage.

The aptamer-conductive particle conjugate includes the amyloid protein oligomer-binding aptamer and thus may specifically bind to an amyloid protein oligomer via an aptamer portion thereof. In addition, since the conjugate includes the conductive particles, the conductive particles may produce heat by high frequency induction heating, thereby generating heat. Use of the aptamer-conductive particle conjugate allows the local heating of only a region irradiated with a high frequency alternating magnetic field, so that a target substance binding to the aptamer may be destroyed by controlling the heat generated. In this manner, since a targeted amyloid protein oligomer is destroyed, accumulation of the amyloid protein oligomer may be prevented or eliminated, thereby allowing the reduction of various symptoms or the prevention of disease due to accumulated amyloid protein oligomer.

The raw material of the conductive particles is not particularly limited as long as the material produces heat by high frequency induction heating. Examples of the raw material include metals, conductive polymers and the like. Preferable examples of the metals include transition metals such as gold, aluminium, copper, and silver, among which gold is particularly preferable.

In a case of using gold particles as the conductive particles, a gold nanoparticle complex may be used. Examples of the gold nanoparticle complex include commercially available gold nanoparticle complexes such as NANOGOLD (trademark) (Nanoprobes Inc.). Gold nanoparticles are advantageous in that optical signal amplification may be made by silver ions and it is possible to establish a detection method for observing color change due to aggregation. Therefore, by binding gold nanoparticles to the aptamer, protein detection with high sensitivity may be achieved.

Additionally, instead of the conductive particles, magnetic particles may be used. As used herein, the magnetic particles may include, for example, materials such as $Fe_2O_3$ and $Fe_3O_4$.

As a method for producing the aptamer-conductive particle conjugate, a method usually used to bind an inorganic material to nucleotide or the like may be applied without any change. Examples of the method include a method for reacting a thiol-modified aptamer with maleimide-containing gold particles.

The high frequency induction heating may be achieved, for example, by an apparatus in which a predetermined electric control circuit includes an impedance matching circuit for amplifying an output from a signal generator to supply to an electromagnetic radiation coil.

The aptamer-conductive particle conjugate may be produced, for example, as follows:

To 30 nmol of gold nanoparticles (diameter: 1.4 nm) is added 100 µl of isopropanol to obtain a mixture. The mixture is diluted to 1/10 with Mili-Q water so that the mixture has a total amount of 1000 µl (a gold nanoparticle solution). Next, 3 nmol of the amyloid protein oligomer-binding aptamer is added to the gold nanoparticle solution, followed by incubation at 4° C. for 24 hours. Next, the resulting mixed solution is subjected to gel filtration chromatography using a gel filtration column (SUPLEX 7516/60) equilibrated with 5 mM $NaH_2PO_4$, 150 mM NaCl, and pH 6.5. Then, desalting and freeze-drying of a fraction obtained by the gel filtration chromatography are performed to prepare an aptamer-gold particle complex.

EXAMPLES

Examples of the present invention will be described below, but the present invention is not limited thereto. Unless otherwise stated, "%" represents percent by mass.

Example 1

Production of α-Synuclein Oligomer-Specific Aptamer (1) Preparation of α-synuclein sample
(1-1) Preparation of monomer

*E. Coli* BL21 (DE3)/pET-28a(+)α-synuclein possessing a plasmid including an α-synuclein gene was cultured in an LB medium containing kanamycin having a final concentration of 30 µg/ml and IPTG was added thereto to induce the expression of α-synuclein. The obtained wet cells were suspended, then crushed, and centrifuged (15,000 g, 4° C., 20 min) to collect the supernatant. The obtained supernatant was heated in boiling water for 20 minutes. After heating, centrifugation (15,000 g, 4° C., 15 min) was performed to remove protein denatured and aggregated due to heat. The obtained supernatant was dialyzed overnight with 20 mM Tris-HCl (pH 8.0). After the dialysis, micro ultracentrifugation was performed (150,000 g, 4° C., 20 min) to obtain the supernatant, and then, the supernatant was purified by FPLC using an anion exchange column RESOURCE Q (GE Healthcare Limited) 6 ml. Two buffers, a buffer A (20 mM Tris-HCl, pH 8.0) and a buffer B (20 mM Tris-HCl, pH 8.0, 0.1 M NaCl), were used. A step-by-step gradient was used, and flow rate, fraction volume, and the like were determined according to manual and column volume to perform purification.

A peak fraction obtained was subjected to protein concentration measurement by a Lowry method. Then, SDS-PAGE was performed to confirm the degree of the purification. After the confirmation of the purification degree, dialysis was performed with Mili-Q or PBS (8.1 mM $Na_2HPO_4$, 1.4 mM $KH_2PO_4$, 37 mM NaCl, 2.7 mM KCl, pH 7.3). The obtained sample was used as an α-synuclein monomer.

(1-2) Preparation of Oligomer

α-synuclein subjected to recombinant expression and purification was dialyzed with Mili-Q, and the α-synuclein after the dialysis was dispensed at 4 to 6 mg and freeze-dried. After that, the freeze-dried sample was rehydrated with Mili-Q to a concentration of 30 mg/ml and stirred for about 30 to 60 minutes for sufficient dissolution, followed by freeze-drying again. Then, the sample was rehydrated with a PBS buffer solution to a concentration of 30 mg/ml and stirred for about 30 to 60 minutes for sufficient dissolution. The resulting sample was purified by gel filtration chromatography using SUPERDEX 200 10/300 column (GE Healthcare Limited). The separation was performed using PBS buffer solution as buffer at a flow rate of 0.5 ml/min. After the separation, a fraction expected to include oligomer was collected and condensed using an ultrafiltration filter (MWCO 100 kDa). After the condensation, sodium azide was added to give a final concentration of 0.02% and the sample was stored at 4° C. The resulting sample was used as an α-synuclein oligomer sample.

(1-3) Preparation of Fibril Sample

The α-synuclein monomer was dissolved at 1 to 2 mg/ml in a PBS buffer solution and the obtained solution was incubated while shaking at 37° C. to promote fibril formation. A fibril sample of α-synuclein was prepared using, as an indicator, fluorescence of an amyloid fibril-binding fluorescent dye Thioflavin T (TfT) (Sigma Aldrich Company). While measuring fluorescent intensity of the TfT, incubation was performed and stopped when the fluorescence of the TfT was saturated. The incubated sample was centrifuged (10,000 g, 20° C., 10 min) to collect the supernatant.

To the pellets was added 400 µl of a PBS buffer solution and the obtained solution was thoroughly vortex-stirred. Then, the solution was centrifuged again under the same conditions and the pellets were washed in the same manner. This operation was repeated three times and the finally obtained pellets were suspended in 50 µl of a PBS buffer solution. The obtained suspension was used as an α-synuclein fibril sample. A protein concentration of the collected supernatant was measured to calculate a protein concentration of the fibril sample, whereby a concentration of the α-synuclein fibril sample was calculated.

Since the fibril sample is unpurified, a slight amount of α-synuclein oligomer seems to be contained therein.

(2) Preparation of α-Synuclein Oligomer-Specific Aptamer
(2-1) Synthesis of Oligonucleotide Each of a random library and primers (SEQ ID NOs: 19 to 23) indicated in the following (a) to (e) was designed to synthesize each oligonucleotide. In the random library and forward primers, an FITC sequence (represented as "FITC" in the following base sequences) was added to the 5' end thereof, and in a reverse primer, a biotin sequence (represented as "Biotin" in the following base sequence) was added to the 3' end thereof, thereby constructing each sequence modified with FITC or Biotin. In addition, regarding a complementary strand for the 3'-end primer region, a complementary strand having a FITC-modified sequence at the 5' end thereof and an unmodified complementary strand were each produced.

(a) Random library (SEQ ID NO: 19)

5'-FITC-ATA CTG CCA TTC ATT TCA TTT (N₂₄) TTT AGA TAT CAG CAT GTG TCA-3'

(b) Complementary strand for the 5'-end primer region (SEQ ID NO: 20)

5'-TGA AAT GAA TGG CAG TAT-3'

(c) Complementary strand for the 3'-end primer region (SEQ ID NO: 21)

5'-TGA CAC ATG CTG ATA TCT-3'

(d) Forward primer (SEQ ID NO: 22)

5'-FITC-ATA CTG CCA TTC ATT TCA-3'

(e) Reverse primer (SEQ ID NO: 23)

5'-TGA CAC ATG CTG ATA TCT-Biotin-3'

(2-2) Screening Using Gel-Shift Assay (Rounds 1 and 2)

The obtained oligonucleotides were screened using a gel-shift assay. In the screening, the following operations (i) to (iv) were repeated twice in total.

(i) Selection of ssDNA Binding to α-Synuclein Oligomer and Confirmation of Binding of ssDNA Library A DNA library modified with FITC at the 5' end thereof and a complementary strand DNA for the primer region were mixed together in an equivalent molar ratio and DNA folding was performed in an TBS buffer solution (10 mM Tris-HCl, 150 mM NaCl, 5 mM KCl, pH 7.4). Then, α-synuclein oligomer and the DNA were mixed together and incubated at room temperature for 1 hour while stirring using a high speed shaker. The folding was carried out by heating at 95° C. for 3 minutes and then reducing the temperature to 25° C. in 30 minutes.

After that, the mixed solution was subjected to electrophoresis using a 3% agarose gel in a TAE buffer solution. Fluorescence of FITC was detected by a variable image analyzer TYHOON 8600 (GE Healthcare Limited, hereinafter the same) to confirm the binding of the oligomer to the DNA. Then, the gel was CBB-stained to observe the protein position.

(ii) Extraction of ssDNA Binding to α-Synuclein Oligomer

From the gel migrated in the mixed solution of the α-synuclein oligomer and the DNA used in the (i) above, a gel of the protein portion was cut out and collected using a cutter and tweezers cleansed with alcohol and burnt at the tips.

From the collected gel, DNA bound to α-synuclein oligomer was extracted using the MERmaid Kit (Q-biogene Co., Ltd). Experiment operation was performed according to an usual protocol. Finally, DNA was eluted in a 1×TE buffer (10 mM Tris-HCl, 1 mM EDTA) and used as a template for the next library.

(iii) Amplification of Extracted ssDNA

PCR was performed using the extracted DNA as a template. Thirty bottles of a PCR reaction solution (100 µl) including a FITC-modified 5' primer (final concentration: 0.4 µM), a Biotin-modified 3' primer (final concentration: 0.4 µM), a dNTP (final concentration: 0.2 mM), 5 U/µl of Taq DNA polymerase, and 5 µl of the template DNA were prepared.

Using a thermal cycler, heating was performed at 95° C. for 3 minutes, at 95° C. for 1 minute, 52° C. for 1 minute, and 72° C. for 1 minute, which was set as 1 cycle and repeated for 30 cycles. Each PCR product was subjected to electrophoresis on a 3% agarose 21 gel in a TAE buffer to confirm the amplification of the DNA as template.

(iv) Single-Stranding of Amplified dsDNA

An amount of 120 µl of avidin-immobilized agarose was washed twice with a column buffer (30 mM HEPES, 500 mM NaCl, 5 mM EDTA, pH 7.0) in an amount of 5 times the amount thereof. To this, to the PCR product was added ×50 TE buffer in an amount of 1/10 times the amount thereof and 5 M NaCl in an amount of 1/5 times the amount thereof, and the obtained solution was added to the washed avidin-immobilized agarose, followed by incubation for 30 minutes.

After the incubation, the supernatant was removed and the agarose was washed twice with a column buffer in an amount of 5 times the amount of the agarose. Next, 0.15M NaOH in an amount of 1.5 times the amount of the agarose was added and stirred for 10 minutes. After collecting the supernatant, again, 0.15M NaOH in the same amount was added to the agarose and stirred for 10 minutes, whereby ssDNA was eluted and the supernatant was collected. The supernatant containing the ssDNA was neutralized with 2M HCl and the ssDNA was collected by ethanol precipitation.

The obtained pellets were dissolved in 60 µl of TE buffer and absorption at 260 nm was measured using a spectrophotometer to calculate DNA concentration. These operations were all performed at room temperature.

(2-3) Competitive Screening Using Aptamer Blotting (Rounds 3, 4, and 5)

The following operations (v) to (viii) were repeated to perform a competitive screening using aptamer blotting for 3 rounds in total.

(v) Selection of ssDNA Binding to α-Synuclein Oligomer

Each of α-synuclein monomer, oligomer, and fibril prepared in various amounts was immobilized on a nitrocellulose membrane and dried. Then, the membrane were incubated with 4% skim milk prepared with TBS-T (25 mM Tris-HCl, pH 7.4, 0.15 M NaCl, 0.005 M KCl, 0.05% Tween 20) at room temperature for 1 hour to perform blocking After that, the membrane was washed with a sufficient amount of TBS-T (2 min×twice and 10 min×one time). The DNA library modified with the FITC at the 5' end was folded in the same manner as in above (i). The DNA and the membrane were incubated at room temperature for 1 hour and then the membrane was washed with a sufficient amount of TBS-T (2 min×twice, 10 min×one time, and 5 min×twice).

(iv) Extraction of ssDNA Binding to α-Synuclein Oligomer

A portion of the nitrocellulose membrane including the immobilized oligomer was cut out and 200 μl of 8M urea and 600 μl of phenol/chloroform were added thereto, stirred for 3 minutes and allowed to stand for 30 minutes at room temperature. To the resulting solution, 100 μl of Milli-Q water was added, and the obtained solution was stirred for 3 minutes and centrifuged (12000 rpm, 10 to 20° C.). The obtained supernatant was transferred to a new Eppen tube. The ssDNA molecules included therein were collected by ethanol precipitation and the resulting pellets were dissolved in 30 μl of TE buffer (10 mM Tris, 1 mM EDTA).

(vii) Amplification of Extracted ssDNA

Operation was performed in the same manner as the (iii).

(viii) Single-Stranding of Amplified dsDNA

Operation was performed in the same manner as the (iv).

(2-4) Sequence Analysis of Obtained Library

DNA extracted at screening of the 4th round or 5th round described above was used as a template to perform PCR using unmodified primers. The resulting PCR product was subjected to electrophoresis on 3% agarose gel in TAE buffer. Then, a band corresponding an intended size was cut out to perform gel purification using MERmaid Kit.

After the purification, the sample band was used for TA cloning and ligated with pGEM-T. The TA cloning was performed using a pGEM-T Vector System. Then, 3 μl of the solution including purified ssDNA, 5 μl of Rapid Ligation Buffer, 1 μl of pGEM-T Vector (50 ng), and 1 μl of T4 DNA Ligase were added and prepared in a total amount of 10 μl, followed by ligation at room temperature for 1 hour.

E. coli DH5α was transformed using a ligation sample, pre-cultured for 1 hour on a shaker, and plated on an LB medium plate containing 100 μg/ml of ampicillin, 0.1 mM of IPTG, and 40 μg/ml of X-gal to perform main culture at 37° C. A colony including the plasmid with the intended DNA introduced therein was selected by color selection.

The E. coli DH5α including the intended DNA was cultured on 1 ml LB liquid medium (Amp. 100 μg/ml) and then, the cells were collected to perform plasmid extraction by an alkali-SDS method. The extracted plasmid was used for sequence analysis.

(2-5) Binding Assay by Aptamer Blotting

α-synuclein monomer, oligomer, and fibril (1 μg) was immobilized on a nitrocellulose membrane and dried. Then, the membrane was incubated with 4% skim milk prepared using TBS-T (25 mM Tris-HCl, pH 7.4, 0.15 M NaCl, 0.005 M KCl, 0.05% Tween-20) at room temperature for 1 hour for blocking. After that, the membrane was washed with a sufficient amount of TBS-T (2 min×twice and 10 min×one time). The obtained plural oligonucleotides modified with FITC at the 5' end (f.c. 100 nM) were folded, and the DNA and the membrane were incubated at room temperature for 1 hour. Next, the membrane was washed with a sufficient amount of TBS-T (2 min×twice, 10 min×one time, and 5 min×twice). After that, an HRP-modified anti-FITC antibody diluted to 1000 times with TBS-T and the membrane were incubated at room temperature for 1 hour and the membrane was washed with a sufficient amount of TBS-T (2 min×twice, 10 min×one time, and 5 min×twice). ECL Plus Western blotting detection reagents (GE Healthcare Ltd.) were added to the membrane, and HRP chemiluminescence was detected by TYPHOON 8600 to observe the binding of the DNA to the protein.

FIG. 1 illustrates the results.

As illustrated in FIG. 1, production of the following eight α-synuclein oligomer-binding aptamers binding not to α-synuclein monomer but strongly binding to α-synuclein oligomer were able to be confirmed.

|         |                              |
|---------|------------------------------|
| T-SO517: | GGTGGCTGGAGGGGCGCGAACG (SEQ ID NO: 1) |
| T-SO606: | GGGTCGGCTGTCCGTGGGTGGGGA (SEQ ID NO: 2) |
| T-SO554: | CGAGGGGCGTCTGGGAGTGGTCGG (SEQ ID NO: 3) |
| T-SO530: | GGTGCGGCGGGACTAGTGGGTGTG (SEQ ID NO: 4) |
| T-SO552: | GCGTGTGGGGCTTGGGCAGCTGGG (SEQ ID NO: 5) |
| T-SO504: | CAGGGGTGGGCAAAGGGCGGTGGTG (SEQ ID NO: 6) |
| T-SO508: | GCCTGTGGTGTTGGGGCGGGTGCG (SEQ ID NO: 7) |
| T-SO602: | GCGGTAGGGTGTGAGCGGAAGGGG (SEQ ID NO: 8) |

Further, the obtained α-synuclein oligomer-binding aptamers were confirmed to have a G-quartet structure using CD spectra.

Specifically, each aptamer was prepared in an amount of 20 μM with TBS buffer (10 mM Tris-HCl, 150 mM NaCl, 5 mM KCl, pH 7.4) and folded. Then, CD spectra were measured using a circular dichroism spectrometer J-720. The measurement was performed under conditions: temperature 20° C., wavelength from 200 to 320 nm, scan rate 100 nm/min, and accumulated number of times 10 times.

As a result, the presence of a minimum value near 240 nm and a maximum value near 260 nm indicated that the above α-synuclein oligomer-binding aptamers have a G-quartet structure.

(3) Confirmation of Specificity of α-Synuclein Oligomer-Binding Aptamer

Among the obtained aptamers, T-SO517 and T-SO606 were compared with an anti-α-synuclein oligomer antibody A11 (Life technologies Corp.) regarding the binding ability.

On the same nitrocellulose membrane, 5 pmol of each of glucose dehydrogenase (PQQGDH) dependent on the coenzyme PQQ, a C-reactive protein (CRP) (Polyscience Corp.), luciferase, and an IgG antibody (Sigma Aldrich Company), and 0.5 μg of α-synuclein oligomer were immobilized. Using the membrane, specificity evaluation was performed by an aptamer blotting method.

In addition, using the anti-oligomer antibody A11, the specificity was evaluated in the same manner. Operation was performed according to a usual protocol. The luciferase used was one prepared by recombinant production using E. coli.

FIG. 2 illustrates the results. In addition, PQQGDH, CRP, luciferase, IgG antibody, and α-synuclein oligomer are all β-structure-rich proteins.

As illustrated in FIG. 2, the A11 antibody had the ability to bind not only to α-synuclein oligomer but also to other β-structure-rich proteins, whereas the T-SO517 and the T-SO606 obtained in Example 1 did not bind to the other proteins and exhibited high specificity to α-synuclein oligomer.

(4) Binding Ability to β Amyloid Peptide

The binding ability of the eight aptamers obtained above to β amyloid peptide was confirmed as follows.

(4-1) Preparation of β Amyloid Peptide $A\beta_{1-40}$

As a β amyloid peptide, $A\beta_{1-40}$ (Peptide Institute, Inc) was used. One hundred μL of a solution of $A\beta_{1-40}$ dissolved at a final concentration of 2.5 mg/ml in hexafluoroisopropanol (HFIP) was mixed with 900 μL of Milli Q water and stirred at room temperature. Then, the obtained solution was centrifuged (14,000 g, room temperature, 15 min) and a supernatant was collected. The supernatant was bubbled with Ar gas and then stirred for 24 hours by a high-speed shaker (800 rpm, room temperature). After that, the sample was centrifuged (14,000 g, 4° C., 20 min) and the collected supernatant was condensed by an ultrafiltration filter (MWCO 10 kDa). This was used as an $A\beta_{1-40}$ oligomer sample.

The $A\beta_{1-40}$ solution prepared above was immediately used as an $A\beta_{1-40}$ monomer sample.

An $A\beta_{1-40}$ fibril sample was prepared as follows. First, the $A\beta_{1-40}$ was dissolved at a final concentration of 4.33 mg/ml in DMSO to prepare a stock solution. The stock solution was diluted to 50 μM with PBS and stirred at 37° C. for about 9 days. After that, the solution was centrifuged at 14,000 G and at 4° C. for 20 minutes and pellets were collected. To the pellets was added 500 μL of PBS, and the operations of stirring and centrifugation were repeated twice to wash the pellets. Absorbance at 280 nm of the supernatant obtained in each operation was measured in the same manner as above to calculate an amount of protein remaining in the pellets. Then, the pellets were rehydrated with PBS to a desired concentration and used as a fibril sample in experiment.

(4-2) Aptamer Blotting Assay

The $A\beta_{1-40}$ monomer, oligomer, and fibril, 12.5 pmol for each, were immobilized on the same nitrocellulose membrane and 500 nM of each aptamer was used to evaluate binding specificity by aptamer blotting. As a control, the A11 was used to perform the same experiment.

The $A\beta_{1-40}$ oligomer sample in amounts of 3 μL, 2 μL, 1 μL, and 0.5 μL and the α-Syn oligomer in amounts of 300 ng 200 ng, 100 ng, and 50 ng, were each immobilized on a nitrocellulose membrane and dot blotting was performed using the A11.

Spot intensities of portions with the immobilized α-Syn oligomer were analyzed to create a calibration curve, whereby an oligomer concentration included in the $A\beta_{1-40}$ oligomer sample was roughly estimated. After that, the $A\beta_{1-40}$ oligomer was immobilized on a nitrocellulose membrane in such a manner that the A11 has the same level of spot intensity, and aptamer blotting was performed using 500 nM of each aptamer. As a control, the A11 was used to perform the same experiment.

FIG. 3 illustrates the results.

As illustrated in FIG. 3, all of the eight amyloid protein oligomer-binding aptamers obtained in Example 1 recognized the $A\beta_{1-40}$ oligomer but did not exhibit the binding ability to the $A\beta_{1-40}$ monomer nor to the $A\beta_{1-40}$ fibril.

Accordingly, the amyloid protein oligomer-binding aptamers according to the present Example were found to specifically recognize α-synuclein oligomer and $A\beta_{1-40}$ oligomer.

Example 2

Binding Ability 1 of Dimeric Aptamer

Sequences of the aptamer T-SO504 obtained in Example 1 were linked via a 5-mer thymidine (t) nucleotide to synthesize an aptamer dimer (504W).

In addition, as comparison controls, a polynucleotide 504M1 (GGGTGGGCAAAGGG: SEQ ID NO:24) was synthesized by deleting three bases of the 5' end and eight bases of the 3' end from the base sequence of the T-SO504, and a polynucleotide 504M2 (GGGCAAAGGG: SEQ ID NO:25) was also synthesized by deleting seven bases of the 5' end and eight bases of the 3' end from the base sequence of the T-SO504.

In each polynucleotide, in order to reduce steric hindrance caused by the binding of the anti-FITC antibody and prevent fluorescence quenching of FITC due to guanine, a 5-mer adenosine (a) nucleotide was added to the 5' end thereof (in T-SO504, a 5-mer thymine (t) nucleotide was added: tT-SO504), and additionally, FITC modification was done. In the 504M1 and the 504M2, furthermore, a 2-mer adenosine nucleotide was added to the 3' end thereof in order to prevent multimer formation.

Table 1 indicates the sequences of the respective aptamers obtained above. In Table 1, the lower-case letters (t or a) represent the added sequences described above.

TABLE 1

| Name | Sequence |
| --- | --- |
| tT-SO504 | tttttCAGGGGTGGGCAAAGGGCGGTGGTG |
| 504M1 | aaaaaGGGTGGGCAAAGGaa |
| 504M2 | aaaaaGGGCAAAGGGaa |
| 504W | aaaaaCAGGGGTGGGCAAAGGGCGGTGGTG tttttCAGGGGTGGGCAAAGGGCGGTGGTG |

The binding abilities of each aptamer to α-synuclein monomer, α-synuclein oligomer, and α-synuclein fibril were performed in the same manner as (2-5) of Example 1 described above. The α-synuclein monomer, α-synuclein oligomer, and α-synuclein fibril used were the same ones as used in Example 1.

FIG. 4 illustrates the results.

As illustrated in FIG. 4, the 504W as a dimer of the T-SO504 obtained in Example 1 exhibited the same specificity as the T-SO504, and the binding ability of the 504W improved.

On the contrary, the 504M1 and the 504M2, respectively, having only three sets and only two sets, respectively, of two consecutive guanosine nucleotides due to the deletion in a part of the base sequence of the T-SO504 were not be able to retain the binding ability of the T-SO504.

Example 3

Binding Ability 2 of Dimeric Aptamer (1) Production of Dimeric Aptamer

A dimer (hereinafter referred to as "5T dimer" or "10T dimer"), in which the sequences of the aptamer T-SO530 obtained in Example 1 were connected in tandem via a 5-mer or 10-mer thymine linker, was designed and synthesized. In each of the aptamers, FITC as an antigen was linked to the 5' end thereof for modification. Between the FITC and the aptamer, a 5-mer thymine was inserted as a linker. Table 2 indicates the sequences of the respective aptamers.

TABLE 2

| Aptamer | Sequence (5' → 3') |
|---|---|
| tT-SO530 | FITC-ttttGGTGCGGCGGGACTAGTGGGTGTG |
| 5T dimer | FITC-ttttGGTGCGGCGGGACTAGTGGGTGTG ttttGGTGCGGCGGGACTAGTGGGTGTG |
| 10T dimer | FITC-ttttGGTGCGGCGGGACTAGTGGGTGTG ttttttttttGGTGCGGCGGGACTAGTGGGTGTG |

(2) Evaluation of Binding Ability of Dimeric Aptamer

The binding abilities of the produced 5T dimer, 10T dimer, and the original aptamer T-SO530 to Aβ oligomer were evaluated.

100 μL of 100 μM of an Aβ oligomer solution or PBS buffer was added to each well of MaxiSorp (registered trademark) plate (Nunc Co., Ltd) and incubated at 37° C. for 1.5 hours to immobilize the Aβ oligomer on the wells. Blocking of each well was performed with a 2% (w/v) BSA solution (TBS-T: 25 mM Tris-HCl, pH 7.4, 0.15M NaCl, 0.005M KCl, 0.05% Tween-20) to produce an Aβ oligomer-immobilized plate.

Figure 5:
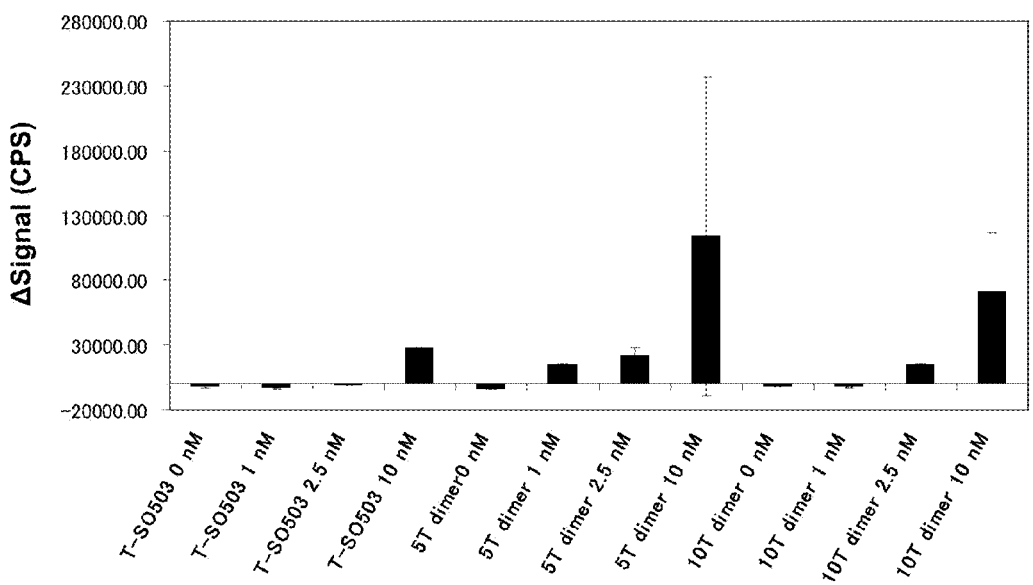
FIG. 5 is a view illustrating the binding ability of respective aptamers according to Example 3 to Aβ protein.

To each well of the Aβ oligomer-immobilized plate was added the each FITC-labeled aptamer prepared in a concentration of 1 nM, 2.5 nM, or 10 nM, and incubation at room temperature for 60 minutes was carried out. After washing the wells, an HRP-modified anti-FITC antibody (Cosmo BiO Co., Ltd) was added to the wells and incubation was performed at room temperature. After washing the wells, an HRP-luminescent substrate was added to detect the binding of each aptamer to the oligomer by chemiluminescence. FIG. 5 illustrates the results.

Further, using the 10T dimer and the original aptamer T-SO530 in a concentration of 1 nM, 2.5 nM, 10 nM, 20 nM, or 60 nM, an experiment for binding the aptamers to the Aβ oligomer was performed in the same manner as above. Based on the obtained binding signals, curve fitting was performed using GraphPad Prism (MDF Co., Ltd.) to calculate a binding dissociation constant (Kd).

As illustrated in FIG. 5, for the T-SO530, a binding signal was confirmed at 10 nM, whereas, for the 5T dimer and the 10T dimer signals were obtained at 1 nM or more and at 2.5 nM or more, respectively. These results indicated that the biding strength of the dimeric aptamers is higher than the monomeric aptamer.

Additionally, regarding the binding dissociation constant (Kd), the Kd of the T-SO530 was 9.03±3.06 nM, and the Kd of the 10T dimer was 1.44±0.68 nM. The Kd value of the dimeric aptamer reduced to about ⅙ as compared to the original aptamer, which indicated that the dimeric aptamer had an improved binding affinity.

(3) Binding Ability to β Amyloid Peptide

The binding abilities of the 5T dimer and the 10T dimer obtained above to β amyloid peptide were confirmed as follows.

(3-1) Preparation Of β Amyloid Monomer

Aβ$_{1-40}$ (Peptide Institute, Inc) was used as a β amyloid peptide. The Aβ$_{1-40}$ was dissolved at a final concentration of 2.5 mg/ml in hexafluoroisopropanol (HFIP) solution to prepare a stock solution. The stock solution diluted to a desired concentration with PBS and immediately used was designated as Aβ$_{1-40}$ monomer. Absorbance at 280 nm of the solution was measured by Ultraviolet-visible spectroscopy system DU 800 (Beckman Coulter Co., Ltd.) or NanoDrop 2000 (Thermo Fisher Scientific Inc.) to confirm protein concentration, whereby the monomer was used as β amyloid monomer in experiment.

(3-2) Preparation of β Amyloid Oligomer

Aβ oligomer was prepared in the same manner as Example 1. Absorbance at 280 nm was measured in the same manner as in the monomeric sample to confirm protein concentration. Then, the oligomer was used as a β amyloid oligomer sample in experiment.

(3-3) Preparation of β Amyloid Fibril

The Aβ$_{1-40}$ was dissolved at a final concentration of 4.33 mg/ml in DMSO to produce a stock solution. The solution was diluted to 50 μM with PBS and stirred at 37° C. for about 9 days. After that, the solution was centrifuged at 14,000 G and at 4° C. for 20 minutes and pellets were collected. To the pellets was added 500 μL of PBS, and the operations of stirring and centrifugation were repeated twice to wash the pellets. Absorbance at 280 nm of the supernatant obtained in each operation was measured in the same manner as above to calculate an amount of protein remaining in the pellets. Then, the pellets were diluted with PBS to a desired concentration and used as a fibril sample in experiment.

(3-4) Aptamer Blotting Assay

The obtained Aβ$_{1-40}$ monomer, oligomer, and fibril sample, 0.5 μg for each, were immobilized on a nitrocellulose membrane and dried. Then, the membrane were incubated with 4% skim milk prepared with TBS-T (0.05% Tween 20) at room temperature for 1 hour for blocking, thereby obtaining a nitrocellulose membrane for blotting assay containing the respective immobilized Aβ$_{1-40}$ samples. On the nitrocellulose membrane, blotting assay was performed in the same manner as the (2-5) of Example 1 except for using 200 nM of each aptamer.

Figure 6:
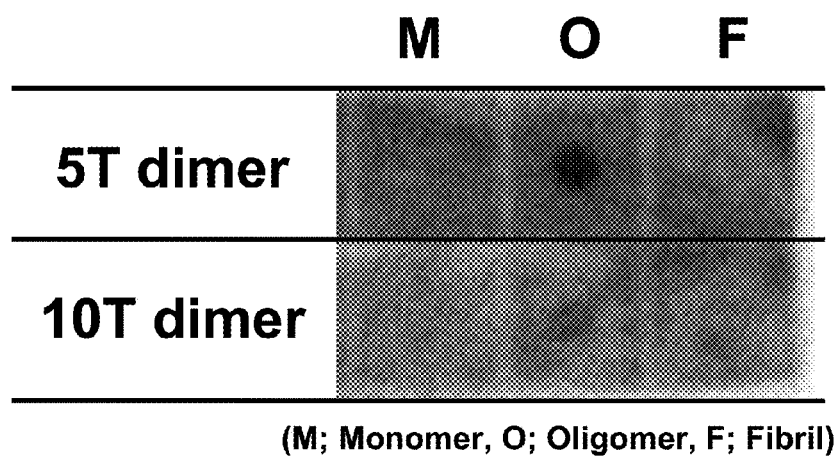
FIG. 6 is a view illustrating the results of an aptamer blotting assay for comparing the binding ability of dimeric aptamers according to Example 3 to β amyloid peptide Aβ$_{1-40}$.

FIG. 6 illustrates the results.

As illustrated in FIG. 6, in each of the 5T dimer and 10T dimer, a strong spot was able to be observed at an oligomer-immobilized position. From the results, both the 5T dimer and 10T dimer were found to exhibit high selectivity to the Aβ$_{1-40}$ oligomer.

Example 4

(1) Production of Modified Sequence

Using, as parent sequences, the sequences of the eight aptamers obtained in Example 1 above, one-point crossover and the introduction of two-base mutation were performed to produce 24 first generation aptamer sequences.

DNAs added an 18-mer complementary strand forming region to the 3' end of each of the obtained first generation aptamer sequences were synthesized. Then, 18-mer DNAs complementary to the above complementary strand forming regions were synthesized and then, FITC was linked to the 5' end thereof by a usual method to produce a labeled sequence, whereby, via the complementary forming region, the first generation aptamer sequences were labeled with FITC. Each of the obtained FITC-labeled aptamers was added to TBS buffer to prepare an FITC-labeled aptamer solution.

100 μL of a 2 μM Aβ oligomer solution or PBS buffer was added to each well of a MaxiSorp (registered trademark) plate (Nunc Co., Ltd) and incubated at 37° C. for 1.5 hours to immobilize the Aβ oligomer on the wells. Blocking of each well was performed with 4% (w/v) skim milk to produce an Aβ oligomer-immobilized plate.

To each well of the Aβ oligomer-immobilized plate was added the each FITC-labeled aptamer prepared in a final concentration of 500 nM, and the wells were incubated at room temperature for 30 minutes.

After washing the wells, an HRP-modified anti-FITC antibody (Cosmo BiO Co., Ltd) was added to the wells and incubation was performed at room temperature. After washing the wells, an HRP luminescent substrate was added to detect and compare the binding of each aptamer to the oligomer by chemiluminescence. For standardization of signal intensity between the respective plates, an aptamer (3'FC508) was used in which FITC was linked to the 3' end of the T-SO508 aptamer sequence as the parent sequence via a complementary strand formation.

Based on the binding ability to the Aβ oligomer, from the first generation aptamers, six sequences having the highest binding ability were selected.

Twenty-four second generation aptamer sequences were produced by one-point crossover and the introduction of two-base mutation using the obtained six first generation aptamer sequences as parent sequences.

Regarding the second generation aptamer sequences, the binding ability to the Aβ oligomer was detected and compared in the same manner as above. Then, four sequences having higher binding ability were selected from the second generation aptamer sequences. A second generation aptamer sequence having the highest binding ability exhibited a chemiluminescence of 8.69 times as much as the binding ability of the parent sequence thereof.

Twenty-four third generation aptamer sequences were produced by one-point crossover and the introduction of two-base mutation using the obtained four second generation aptamer sequences as parent sequences.

Regarding the third generation aptamer sequences, the binding ability to the Aβ oligomer was detected and compared in the same manner as above. A third generation aptamer sequence having the highest binding ability exhibited a chemiluminescence of 22.55 times as much as the binding ability of the parent sequence thereof.

In this manner, the following Aβ oligomer-binding aptamers were obtained:

```
2G16:  CGAGGGGCGTCTGGGGGGGAGGGA  (SEQ ID NO: 9)
2G4:   CGGGGGGCGTGTGGGAGAGGTCGG  (SEQ ID NO: 10)
2G13:  TGGGGGGCGTAGGGTCGCGAACGA  (SEQ ID NO: 11)
2G9:   CGGGGGGCGTAGGGGAGAGGGGCG  (SEQ ID NO: 12)
3G4:   CGGGGGGCCTGAGGGGGGAGGGA   (SEQ ID NO: 13)
3G21:  CGGGGCGCATCTGGGGGGAGGGA   (SEQ ID NO: 14)
3G16:  CGGGGGGCTTGTGGCGGGAGGGA   (SEQ ID NO: 15)
3G22:  CGAGGGGAGTAGGGGGAGGGGCG   (SEQ ID NO: 16)
3G14:  CGGGGGGCGTCTGGGCGCAGGGA   (SEQ ID NO: 17)
3G9:   CGGGGGCCGTTGGGGGGGAGGGA   (SEQ ID NO: 18)
```

(2) Binding Ability Evaluation

From the aptamers obtained in the (1) above, regarding 2G16 and 3G4, as well as the aptamer 3'FC508 obtained from the parent sequences, the binding ability was evaluated.

Figure 7:
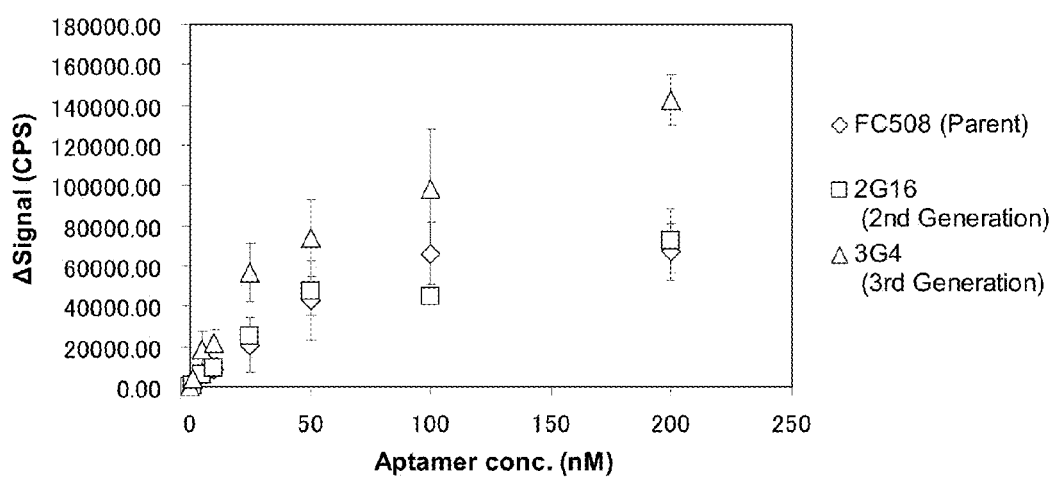
FIG. 7 is a graph illustrating the binding ability of modified aptamers according to Example 4 to Aβ protein.

Specifically, a concentration of each of the aptamers was set to 1 nM, 5 nM, 10 nM [[1 nM]], 25 nM, 50 nM, 100 nM, or 200 nM to confirm the binding ability of the each aptamer to Aβ oligomer, as in the above (1). Based on the obtained binding signals, curve fitting was performed using GraphPad Prism (MDF Co., Ltd.) to calculate a binding dissociation constant (Kd). FIG. 7 illustrates the results. In the respective symbols of FIG. 7, the rhombus represents the 3'FC508, the square represents the 2G16, and the triangle represents the 3G4.

As a result, Kds of the 3'FC508, the 2G16, and the 3G4, respectively, were 67.74 nM, 67.10 nM, and 70.75 nM, respectively. The Kds of the aptamers were all about 70 nM and there was no difference between the binding dissociation constants thereof.

(3) Structural Analysis of Aptamer

Each structure of the aptamers 3'FC508, 2G16, and 3G4 obtained in the above (1) was analyzed by electrophoresis on 15% by mass of polyacrylamide gel. The respective aptamers 3'FC508, 2G16, and 3G4 modified with FITC obtained in the (1) were applied on 15% by mass of Tris-glycine gel (WAKO) and electrophoresis was carried out in TBE buffer. After that, a migration position of each of the aptamers was confirmed by observation of FITC fluorescence.

Figure 8:
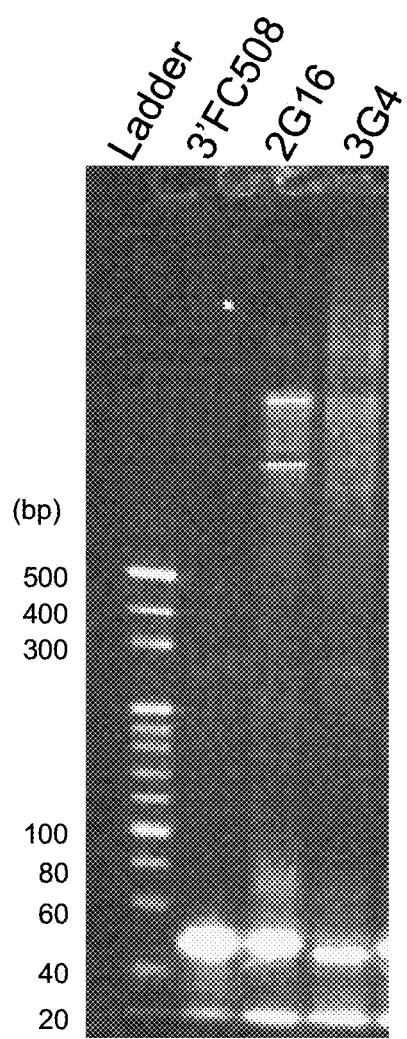
FIG. 8 is an image illustrating the results of PAGE analysis of 2G16 and 3G4 according to Example 4.

FIG. 8 indicates the results of the PAGE analysis. In FIG. 8, respective lanes represent a ladder and the aptamers 3'FC508, 2G16, and 3G4 from the left.

As illustrated in FIG. 8, for both the aptamers 2G16 and 3G4, in addition to a band near 50 bp, plural bands were detected at a migration position estimated to be 1000 bp. From the results, the aptamers 2G16 and 3G4 were found to have not only a monomeric conformation but also a multimeric conformation formed by a gathering of a dozen or more of each aptamer sequence.

In addition, it was found that the in silico maturation under the above-described conditions can produce an aptamer that forms a multimer and binds to protein.

(4) Binding Ability to β Amyloid Peptide

The binding ability of the 2G16 and 3G4 obtained above to β amyloid peptide was confirmed.

As respective samples of β amyloid monomer, oligomer, and fibril, those obtained in Example 3 (3) were used.

Figure 9:
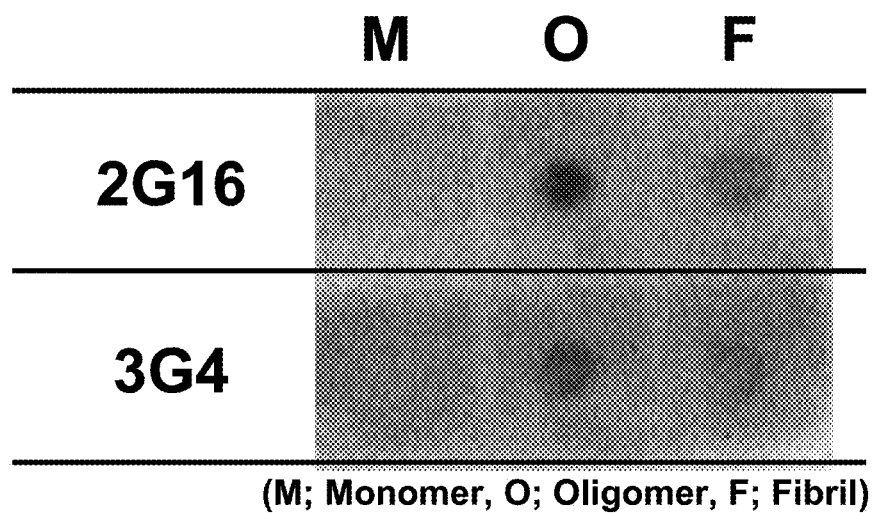
FIG. 9 is a view illustrating the results of an aptamer blotting assay for comparing the binding ability of dimeric aptamers according to Example 4 to β amyloid peptide Aβ$_{1-40}$.

Blotting assay was performed in the same manner as Example 3 (3) except for using each of the aptamers 2G16 and 3G4 in a concentration of 200 nM. FIG. 9 illustrates the results.

As illustrated in FIG. 9, for both the 2G16 and 3G4, spots were able to be observed at positions with immobilized oligomer and fibril, and particularly, at oligomer-immobilized positions, strong spots were able to be observed. On the contrary, for both of the aptamers, no spot was observed at monomer-immobilized positions. From the results, the 2G16 and 3G4 were found to both specifically recognize the oligomer of $A\beta_{1-40}$ compared to the monomer thereof.

Therefore, the amyloid protein oligomer-binding aptamer of the present invention may specifically recognize an amyloid protein oligomer.

The disclosure of Japanese Patent Application No. 2011-033998 filed on Feb. 18, 2011 is incorporated herein by reference in its entirety.

All documents, patent applications, and technical standards described in the present description are incorporated herein by reference to the same extent as if each individual document, patent application, or technical standard were specifically and individually indicated to be incorporated by reference.

The invention claimed is:

1. An aptamer having a G-quartet structure and being at least one selected from the group consisting of the following polynucleotides, the aptamer having a binding ability to an amyloid protein oligomer:
   (1) a polynucleotide comprising a base sequence represented by any one of SEQ ID NO:1 to SEQ ID NO:18;
   (2) a polynucleotide of 20-30 nucleotides in length and comprising a base sequence that includes at least four sets of at least two consecutive guanosine nucleotides and in which one or 2-5 bases have been deleted, substituted, or added in a base sequence represented by any one of SEQ ID NO:1 to SEQ ID NO:18; and
   (3) a polynucleotide that is a multimer including the polynucleotide of (1) or (2) as a structural unit.

2. The aptamer according to claim 1, wherein the polynucleotide (3) includes the polynucleotide of (1) or (2) and a linker sequence of 2-15 nucleotides linking respective polynucleotides of (1) or (2).

3. An amyloid protein oligomer detection kit including the aptamer according to claim 2.

4. An amyloid protein oligomer detection method, the method including contacting the aptamer according to claim 2 with a test sample and detecting a complex of an amyloid protein oligomer and the aptamer in the test sample.

5. The amyloid protein oligomer detection method according to claim 4, wherein the test sample is at least one selected from the group consisting of cerebrospinal fluid, serum, plasma, and dilutions thereof.

6. An amyloid protein oligomer detection kit including the aptamer according to claim 1.

7. An amyloid protein oligomer detection method, the method including contacting the aptamer according to claim 1 with a test sample and detecting a complex of an amyloid protein oligomer and the aptamer in the test sample.

8. The amyloid protein oligomer detection method according to claim 7, wherein the test sample is at least one selected from the group consisting of cerebrospinal fluid, serum, plasma, and dilutions thereof.

9. The aptamer according to claim 1, wherein the polynucleotide of (2) is 23-25 nucleotides in length and comprises 14-15 guanosine in its sequence.

10. The aptamer according to claim 1, wherein the aptamer is a DNA.

11. A polynucleotide comprising a base sequence represented by any one of SEQ ID NO:1 to SEQ ID NO:18.

12. A polynucleotide that is a multimer including, as a structural unit, a polynucleotide including a base sequence represented by any one of SEQ ID NO:1 to SEQ ID NO:18.

* * * * *

SEQUENCE LISTING

<160> NUMBER OF SEQ ID NOS: 25

<210> SEQ ID NO 1
<211> LENGTH: 23
<212> TYPE: DNA
<213> ORGANISM: Artificial Sequence
<220> FEATURE:
<223> OTHER INFORMATION: synthetic polynucleotide T-SO517

<400> SEQUENCE: 1
ggtggctgga gggggcgcga acg                                              23

<210> SEQ ID NO 2
<211> LENGTH: 24
<212> TYPE: DNA
<213> ORGANISM: Artificial Sequence
<220> FEATURE:
<223> OTHER INFORMATION: synthetic polynucleotide T-SO606

<400> SEQUENCE: 2
gggtcggctg tccgtgggtg ggga                                             24

<210> SEQ ID NO 3
<211> LENGTH: 24
<212> TYPE: DNA
<213> ORGANISM: Artificial Sequence
<220> FEATURE:
<223> OTHER INFORMATION: synthetic polynucleotide T-SO554

<400> SEQUENCE: 3
cgaggggcgt ctgggagtgg tcgg                                             24

<210> SEQ ID NO 4
<211> LENGTH: 24
<212> TYPE: DNA
<213> ORGANISM: Artificial Sequence
<220> FEATURE:
<223> OTHER INFORMATION: synthetic polynucleotide T-SO530

<400> SEQUENCE: 4
ggtgcggcgg gactagtggg tgtg                                             24

<210> SEQ ID NO 5
<211> LENGTH: 24
<212> TYPE: DNA
<213> ORGANISM: Artificial Sequence
<220> FEATURE:
<223> OTHER INFORMATION: synthetic polynucleotide T-SO552

<400> SEQUENCE: 5
gcgtgtgggg cttgggcagc tggg                                             24

<210> SEQ ID NO 6
<211> LENGTH: 25
<212> TYPE: DNA
<213> ORGANISM: Artificial Sequence
<220> FEATURE:
<223> OTHER INFORMATION: synthetic polynucleotide T-SO504

<400> SEQUENCE: 6
caggggtggg caaagggcgg tggtg                                            25

<210> SEQ ID NO 7
<211> LENGTH: 24
<212> TYPE: DNA
<213> ORGANISM: Artificial Sequence

```
<220> FEATURE:
<223> OTHER INFORMATION: synthetic polynucleotide T-SO508

<400> SEQUENCE: 7
gcctgtggtg ttggggcggg tgcg                                          24

<210> SEQ ID NO 8
<211> LENGTH: 24
<212> TYPE: DNA
<213> ORGANISM: Artificial Sequence
<220> FEATURE:
<223> OTHER INFORMATION: synthetic polynucleotide T-SO602

<400> SEQUENCE: 8
gcggtagggt gtgagcggaa gggg                                          24

<210> SEQ ID NO 9
<211> LENGTH: 24
<212> TYPE: DNA
<213> ORGANISM: Artificial Sequence
<220> FEATURE:
<223> OTHER INFORMATION: synthetic polynucleotide 2G16

<400> SEQUENCE: 9
cgaggggcgt ctggggggga ggga                                          24

<210> SEQ ID NO 10
<211> LENGTH: 24
<212> TYPE: DNA
<213> ORGANISM: Artificial Sequence
<220> FEATURE:
<223> OTHER INFORMATION: synthetic polynucleotide 2G4

<400> SEQUENCE: 10 cgggggcgt gtgggagagg tcgg                                           24

<210> SEQ ID NO 11
<211> LENGTH: 24
<212> TYPE: DNA
<213> ORGANISM: Artificial Sequence
<220> FEATURE:
<223> OTHER INFORMATION: synthetic polynucleotide 2G13

<400> SEQUENCE: 11
tggggggcgt agggtcgcga acga                                          24

<210> SEQ ID NO 12
<211> LENGTH: 24
<212> TYPE: DNA
<213> ORGANISM: Artificial Sequence
<220> FEATURE:
<223> OTHER INFORMATION: synthetic polynucleotide 2G9

<400> SEQUENCE: 12
cggggggcgt aggggagagg ggcg                                          24

<210> SEQ ID NO 13
<211> LENGTH: 24
<212> TYPE: DNA
<213> ORGANISM: Artificial Sequence
<220> FEATURE:
<223> OTHER INFORMATION: synthetic polynucleotide 3G4

<400> SEQUENCE: 13
cggggggcct gaggggggga ggga                                          24
```

```
<210> SEQ ID NO 14
<211> LENGTH: 24
<212> TYPE: DNA
<213> ORGANISM: Artificial Sequence
<220> FEATURE:
<223> OTHER INFORMATION: synthetic polynucleotide 3G21

<400> SEQUENCE: 14
cggggcgcat ctgggggga ggga                                        24

<210> SEQ ID NO 15
<211> LENGTH: 24
<212> TYPE: DNA
<213> ORGANISM: Artificial Sequence
<220> FEATURE:
<223> OTHER INFORMATION: synthetic polynucleotide 3G16

<400> SEQUENCE: 15 cgggggggctt gtggcgggga ggga                                      24

<210> SEQ ID NO 16
<211> LENGTH: 24
<212> TYPE: DNA
<213> ORGANISM: Artificial Sequence
<220> FEATURE:
<223> OTHER INFORMATION: synthetic polynucleotide 3G22

<400> SEQUENCE: 16
cgaggggagt aggggggagg ggcg                                       24

<210> SEQ ID NO 17
<211> LENGTH: 24
<212> TYPE: DNA
<213> ORGANISM: Artificial Sequence
<220> FEATURE:
<223> OTHER INFORMATION: synthetic polynucleotide 3G14

<400> SEQUENCE: 17
cggggggcgt ctgggcgcga ggga                                       24

<210> SEQ ID NO 18
<211> LENGTH: 24
<212> TYPE: DNA
<213> ORGANISM: Artificial Sequence
<220> FEATURE:
<223> OTHER INFORMATION: synthetic polynucleotide 3G9

<400> SEQUENCE: 18
cgggggccgt tggggggga ggga                                        24

<210> SEQ ID NO 19
<211> LENGTH: 66
<212> TYPE: DNA
<213> ORGANISM: Artificial Sequence
<220> FEATURE:
<223> OTHER INFORMATION: synthetic random library oligonucleotide
<220> FEATURE:
<221> NAME/KEY: misc_feature
<222> LOCATION: (22)..(45)
<223> OTHER INFORMATION: n is a, c, g, t or absent

<400> SEQUENCE: 19
atactgccat tcatttcatt tnnnnnnnnn nnnnnnnnnn nnnntttag atatcagcat    60 gtgtca                                                             66
```

```
<210> SEQ ID NO 20
<211> LENGTH: 18
<212> TYPE: DNA
<213> ORGANISM: Artificial Sequence
<220> FEATURE:
<223> OTHER INFORMATION: synthetic 5' primer

<400> SEQUENCE: 20
tgaaatgaat ggcagtat                                                 18

<210> SEQ ID NO 21
<211> LENGTH: 18
<212> TYPE: DNA
<213> ORGANISM: Artificial Sequence
<220> FEATURE:
<223> OTHER INFORMATION: synthetic 3' primer

<400> SEQUENCE: 21
tgacacatgc tgatatct                                                 18

<210> SEQ ID NO 22
<211> LENGTH: 18
<212> TYPE: DNA
<213> ORGANISM: Artificial Sequence
<220> FEATURE:
<223> OTHER INFORMATION: synthetic forward primer

<400> SEQUENCE: 22
atactgccat tcatttca                                                 18

<210> SEQ ID NO 23
<211> LENGTH: 18
<212> TYPE: DNA
<213> ORGANISM: Artificial Sequence
<220> FEATURE:
<223> OTHER INFORMATION: synthetic reverse primer

<400> SEQUENCE: 23
tgacacatgc tgatatct                                                 18

<210> SEQ ID NO 24
<211> LENGTH: 14
<212> TYPE: DNA
<213> ORGANISM: Artificial Sequence
<220> FEATURE:
<223> OTHER INFORMATION: synthetic polynucleotide 504M1

<400> SEQUENCE: 24
gggtgggcaa aggg                                                     14

<210> SEQ ID NO 25
<211> LENGTH: 10
<212> TYPE: DNA
<213> ORGANISM: Artificial Sequence
<220> FEATURE:
<223> OTHER INFORMATION: synthetic polynucleotide 504M2

<400> SEQUENCE: 25
gggcaaaggg                                                          10
```